United States Patent [19]
Fischell et al.

[11] Patent Number: 6,013,019
[45] Date of Patent: Jan. 11, 2000

[54] TEMPORARY RADIOISOTOPE STENT

[75] Inventors: Robert E. Fischell, Dayton, Md.;
David R. Fischell, Fair Haven, N.J.;
Tim A. Fischell, Richland, Mich.

[73] Assignee: IsoStent, Inc., Belmont, Calif.

[21] Appl. No.: 09/055,484

[22] Filed: Apr. 6, 1998

[51] Int. Cl.[7] .............................. A61N 5/00; A61M 29/00
[52] U.S. Cl. .................. 600/3; 600/1; 604/104;
606/191; 606/194; 606/108; 606/198
[58] Field of Search ........................ 600/3, 11; 604/93,
604/96, 97, 280, 101, 104; 606/194, 108,
198, 191, 192

[56] References Cited

U.S. PATENT DOCUMENTS

| | | | |
|---|---|---|---|
| 5,034,001 | 7/1991 | Garrison et al. | 604/53 |
| 5,059,166 | 10/1991 | Fischell et al. | 600/3 |
| 5,213,561 | 5/1993 | Weinstein et al. | 600/3 |
| 5,411,466 | 5/1995 | Hess | 600/3 |
| 5,441,516 | 8/1995 | Wang et al. | 606/198 |
| 5,449,372 | 9/1995 | Schmaltz et al. | 606/198 |
| 5,540,659 | 7/1996 | Teirstein et al. | 600/3 |
| 5,879,282 | 3/1999 | Fischell et al. | 600/3 |

FOREIGN PATENT DOCUMENTS

0497495A2  8/1992  European Pat. Off. ......... A61N 5/10

*Primary Examiner*—Cary O'Connor
*Assistant Examiner*—Navin Natnithithadha

[57] ABSTRACT

The temporary radioisotope stent catheter system of the present invention includes a temporary radioisotope stent that is situated at a distal portion of two, co-axially situated, thin-walled tubes. The catheter system can be delivered into a vessel of a human body either as a stand-alone device or it can be used in conjunction with an elongated cylindrical sheath which is a form of delivery catheter. If used as a stand-alone device, the temporary radioisotope stent is first percutaneously advanced through a guiding catheter and is then placed at the site of a stenotic dilatation. An operating means located at a proximal portion of the catheter system is then used to increase the diameter of the temporary radioisotope stent to be approximately equal to the inside diameter of the dilated stenosis. The temporary radioisotope stent is then retained at that position for an irradiation time period that is determined by the level of radioactivity of the stent, by the diameter of the dilated stenosis, and by the dose of radiation that is prescribed for application to that portion of the artery. At the conclusion of the irradiation time period, the operating means at the proximal portion of the catheter system is used to decrease the diameter of the temporary radioisotope stent to its minimum value, and then the catheter system is removed from the patient's body.

44 Claims, 12 Drawing Sheets

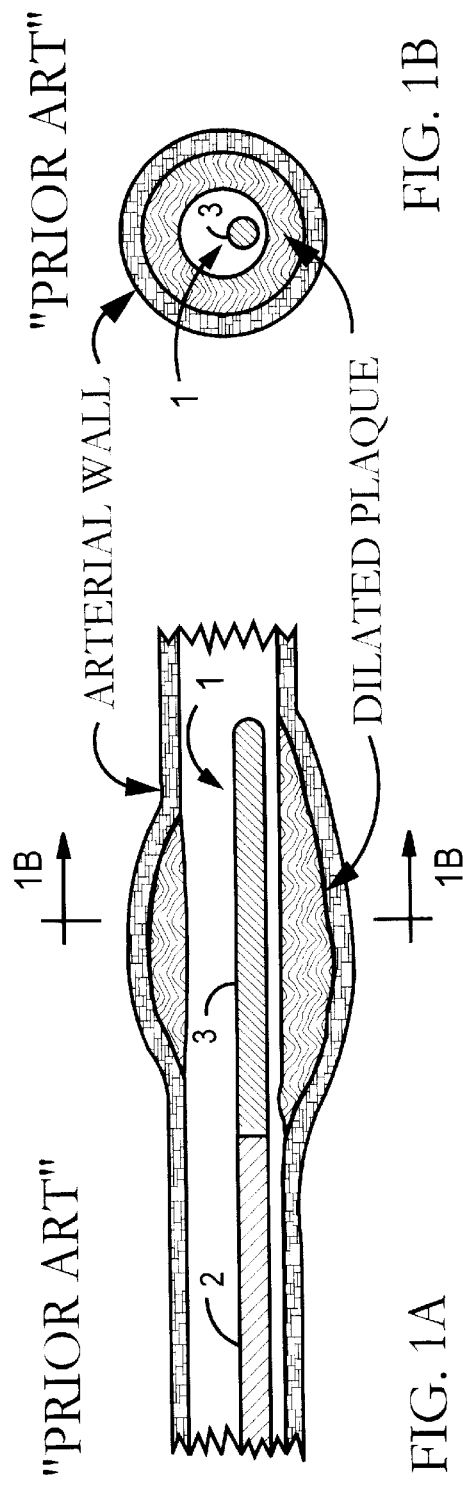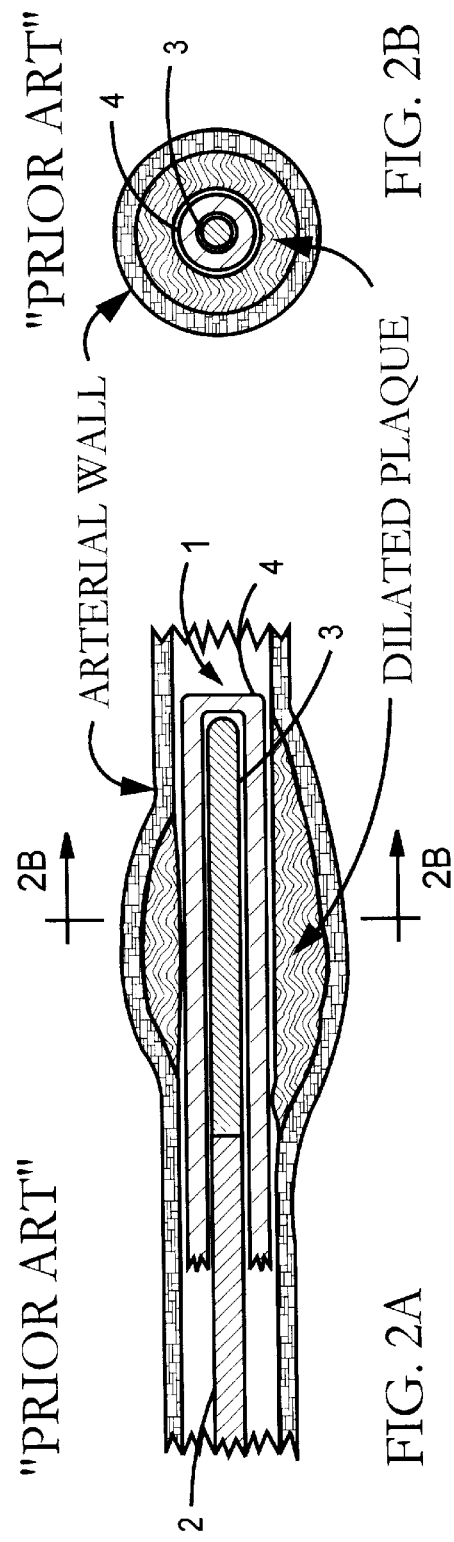

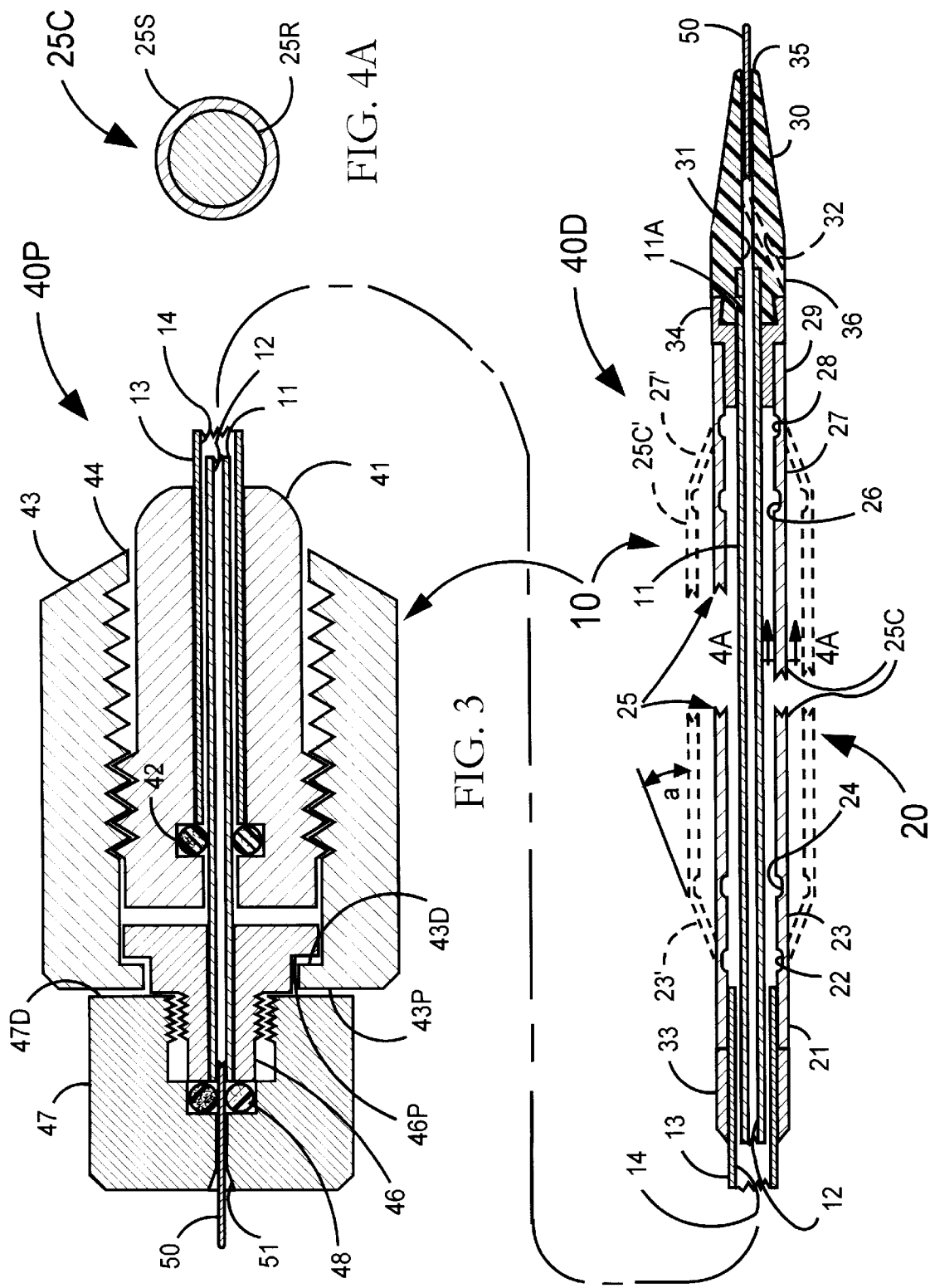

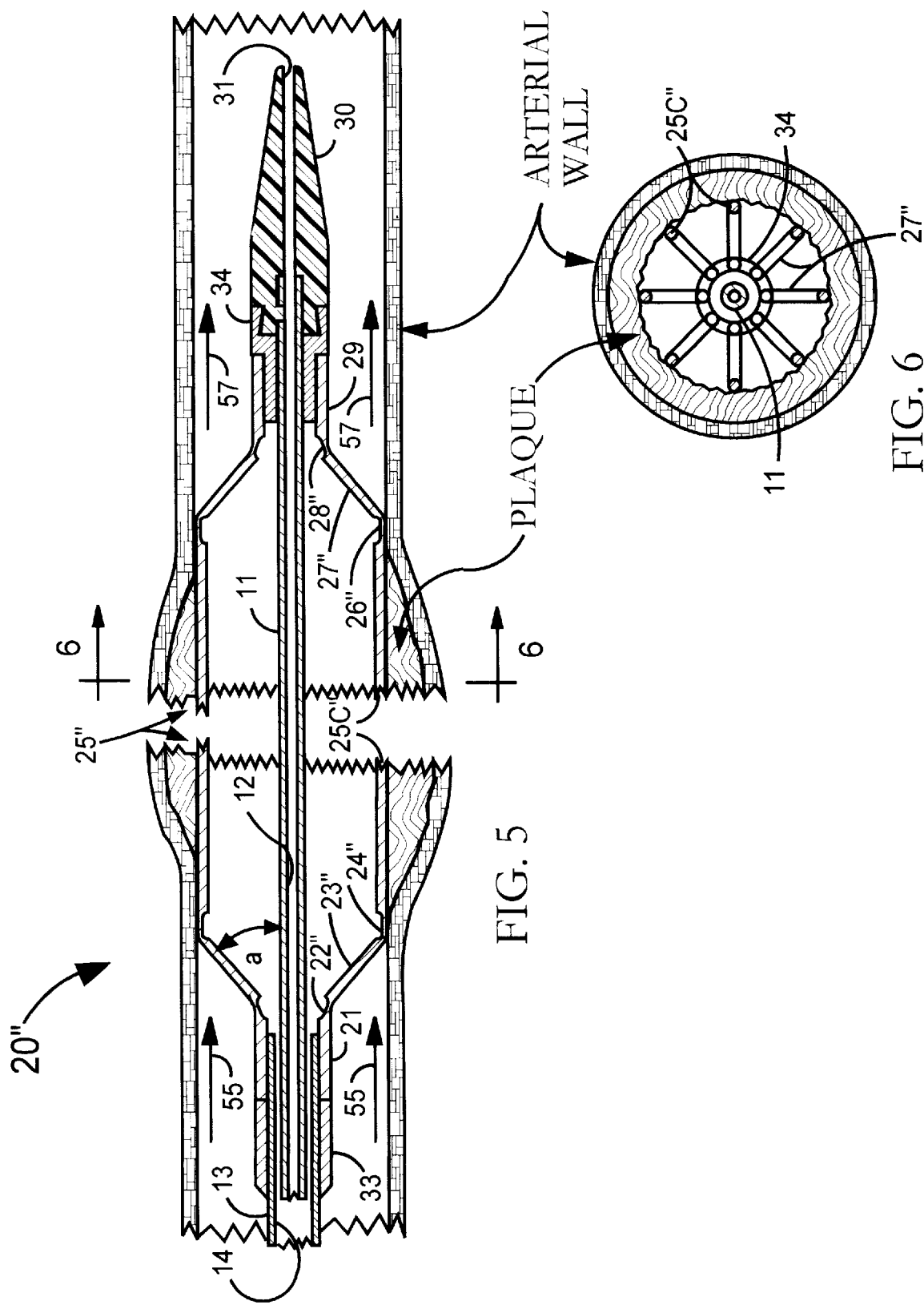

TEMPORARY RADIOISOTOPE STENT

FIELD OF USE

This invention is in the field of percutaneously inserted catheters with radioactive distal sections that are used to decrease the rate of restenosis in arteries subsequent to balloon angioplasty.

BACKGROUND OF THE INVENTION

In U.S. Pat. No. 5,059,166 by R. E. Fischell et al there is described a thin wire with a radioactive tip, which tip can be inserted within an artery of a human subject to irradiate a section of that artery that has been treated with balloon angioplasty. The purpose of that radiation is to decrease the rate of restenosis at the treatment site. A significant disadvantage of a thin wire that is not centered in the artery is that the side of the artery that is touched by the wire will experience a much higher dose of radiation as compared to the opposite side of the artery.

In the same U.S. Pat. No. 5,059,166 by R. E. Fischell et al, there is also described a radioisotope stent that is permanently placed at the site of a stenotic dilatation. Although the radioisotope stent is accurately centered in the artery, animal testing has shown that the permanently implanted radioisotope stent can cause the formation of an acellular matrix within the stent that can result in restenosis.

SUMMARY OF THE INVENTION

The present invention is designed to overcome several of the shortcomings of the prior devices that are intended to irradiate a site in an artery that has been subjected to balloon angioplasty and/or stent implantation. Specifically, the catheter system of the present invention is a temporary radioisotope stent that is situated at a distal portion of two, co-axially situated, thin-walled tubes. The catheter system can be delivered into a vessel of a human body either as a stand-alone device or it can be used in conjunction with an elongated cylindrical sheath which is a form of delivery catheter for the temporary radioisotope stent. If used as a stand-alone device, the temporary radioisotope stent is first percutaneously advanced through a guiding catheter and is then placed at the site of a stenotic dilatation. This positioning is accomplished with the temporary radioisotope stent being maintained at its minimum diameter. Once at the proper position within the dilated stenosis, an operating means located at a proximal portion of the catheter system is then used to increase the diameter of the temporary radioisotope stent to be approximately equal to the inside diameter of the dilated stenosis. The temporary radioisotope stent is then retained at that position for an irradiation time period that is determined by the level of radioactivity of the stent, by the diameter of the dilated stenosis, and by the dose of radiation that is prescribed for application to that portion of the artery. At the conclusion of the irradiation time period, the operating means at the proximal portion of the catheter system is used to decrease the diameter of the temporary radioisotope stent to its minimum value, and then the catheter system is removed from the patient's body.

The catheter system of the present invention can be used with a previously inserted sheath to facilitate the placement of the temporary radioisotope stent at the site of the dilated stenosis. The sheath can have a tapered distal portion to facilitate its introduction over a guide wire, but the tapered distal portion can open to allow the passage of the temporary radioisotope stent through the distal end of the sheath. In an alternative embodiment, the sheath could completely contain the catheter system so that it would not be exposed to the patient's blood. To obtain perfusion during irradiation of the dilated stenosis, an expanded section of the sheath which surrounds the temporary radioisotope stent can be drawn radially inward by applying suction at the proximal end of a closed end sheath.

The distal portion of the catheter system includes radiopaque marker bands located at the proximal end and the distal end of the temporary radioisotope stent which marker bands assist in accurately placing the stent at the correct location within the sheath and within the artery.

Each one of a multiplicity of longitudinal struts of the stent includes a radioactive source. Radiopaque markers are also placed in positions to indicate the extremities of these radioactive sources. Specifically, these radiopaque markers are placed within each longitudinal strut at the distal end and the proximal end of each radioactive source.

Thus it is an object of this invention to (1) have a temporary radioisotope stent catheter system that is adapted to be percutaneously inserted into an artery of a human body, (2) advance the catheter system until a temporary radioisotope stent located at a distal portion of the catheter is placed at the desired irradiation site, (3) expand the diameter of the temporary radioisotope stent until the longitudinal struts of the stent are in contact with or in close proximity to the arterial wall, (4) irradiate that section of the artery with a prescribed dose of radiation from a radioactive source located in the struts of the stent, (5) reduce the diameter of the temporary radioisotope stent, and (6) remove the catheter system from the patient's artery.

Another object of this invention is to have a temporary radioisotope stent catheter system that allows perfusion of distal tissue by means of blood flow through the temporary radioisotope stent when it is deployed.

Still another object of this invention is to have a temporary radioisotope stent catheter system which has the capability of being inserted over a guide wire using the over-the-wire technique.

Still another object of this invention is to have a temporary radioisotope stent catheter system which has the capability of being inserted over a guide wire using a rapid exchange technique.

Still another object of this invention is to have the temporary radioisotope stent located at a distal portion of the catheter system, the stent having a multiplicity of longitudinal struts with a radioactive source situated within each of the struts.

Still another object of this invention is to have a radiopaque marker situated at the proximal end and the distal end of the radioactive source that is located within each longitudinal strut.

Still another object of this invention is to have radiopaque marker bands located at both the proximal end and distal end of the temporary radioisotope stent.

Still another object of this invention is to have the radioactive source in the longitudinal struts of the temporary radioisotope stent be predominately a beta particle emitting radioisotope.

Still another object of this invention is that the radioactive source located within the longitudinal struts is strontium-90 (Sr-90).

Still another object of this invention is that the radioactive source located within the longitudinal struts is phosphorus-32 (P-32).

Still another object of this invention is that the radioactive source in the longitudinal struts is yttrium-90 (Y-90).

Still another object of this invention is to have the temporary radioisotope stent catheter system being adapted to be placed through an elongated, cylindrical sheath which can be percutaneously inserted in the patient's arterial system prior to the insertion of the temporary radioisotope stent catheter system.

Still another object of this invention is that a perfusion sheath can be inserted into a vessel of the human body prior to the insertion of a temporary radioisotope stent catheter system, which sheath has an open expandable section located at a distal portion of the sheath, which expandable portion when expanded allows blood to pass through internal to the expanded section thus allowing perfusion of distal tissue.

Still another object of this invention is that a closed perfusion sheath can be inserted into a vessel of the human body prior to the insertion of a temporary radioisotope stent catheter system, which closed sheath has a closed expandable section located at a distal portion of the sheath, which expandable portion when expanded allows blood to pass through external to the expanded section thus allowing perfusion of distal tissue.

Still another object of this invention is to connect a fluid source at the proximal end of the closed perfusion sheath which fluid source can apply either or both a fluid pressure or suction within the central lumen of the perfusion sheath so as to expand or contract the expandable section of the sheath.

Still another object of this invention is to have a radioisotope stent that includes a radioactive source, which radioactive source does not make direct contact with the blood vessel wall of the dilated stenosis where the stent has been placed.

These and other objects and advantages of this invention will become obvious to a person of ordinary skill in this art upon reading the detailed description of this invention including the associated drawings as presented herein.

BRIEF DESCRIPTION OF THE DRAWINGS

FIG. 1A is a longitudinal cross section of a prior art device which has a radioactive source located at a distal portion of a long thin wire for the purpose of irradiating a dilated stenosis.

FIG. 1B is a transverse cross section of the prior art thin wire with a radioactive source located at a distal portion of the wire at section 1B—1B of FIG. 1A.

FIG. 2A is a longitudinal cross section of a prior art device in which a thin wire having a radioisotope located at a distal portion is centered within the artery and within a closed sheath at a location where balloon angioplasty has been performed.

FIG. 2B is a transverse cross section of the prior art device which is a thin wire having a radioisotope located at a distal portion as would be seen at section 2B—2B of FIG. 2A.

FIG. 3 is a longitudinal cross section of a temporary radioisotope stent catheter system showing details of both a proximal portion and distal portion of the catheter system.

FIG. 4A is a transverse cross section of one of the longitudinal struts of the catheter system as seen at section 4A—4A in FIG. 3.

FIG. 5 is an longitudinal cross section of a distal portion of the temporary radioisotope stent catheter system showing the temporary radioisotope stent in its radially expanded position within a section of an artery that has undergone balloon angioplasty and/or stent implantation.

FIG. 6 is a transverse cross section of the temporary radioisotope stent at section 6—6 of FIG. 5 which shows the longitudinal struts deployed onto the inner surface of the dilated stenosis of an artery.

FIG. 15 is a transverse cross section of the alternative embodiment of the perfusion sheath and the temporary radioisotope stent catheter system at section 15—15 of FIG. 14.

DETAILED DESCRIPTION OF THE INVENTION

FIGS. 1A and 1B illustrate a thin wire 1 having for most of its length a proximal portion 2 and having a distal portion 3 which is a radioactive source that has been placed at a site within an artery where balloon angioplasty has accomplished dilatation of a stenosis by pushing radially outward the plaque that caused the stenosis. As most clearly seen in FIG. 1B, without any centering means, the radioactive source will nearly always make contact with the inner surface of the dilated stenosis. This situation is disadvantageous because the dose of radiation applied at the point of contact will be dramatically greater than a diametrically opposite point on the inner surface of the dilated stenosis. Thus, if the point of contact has the proper radiation dose, the opposite point on the surface of the dilated stenosis will experience an ineffective dose of radiation.

FIGS. 2A and 2B illustrate an improved version of the device that was illustrated in FIGS. 1A and 1B. Specifically, FIGS. 2A and 2B illustrate the same thin wire 1 having a proximal portion 2 for most of its length and a distal portion 3 which is a radioactive source. The closed and centering means 4 provides the capability to have essentially the same radiation dose at all points on the inner surface of the dilated stenosis. However, when the radioactive source is placed in a vessel that has a large diameter, and if the radioactive source is optimized as a pure beta particle emitter, then there would typically be an insufficient number of beta particles reaching most of the arterial wall to provide an adequate radiation dose to that tissue.

Figure 4B:
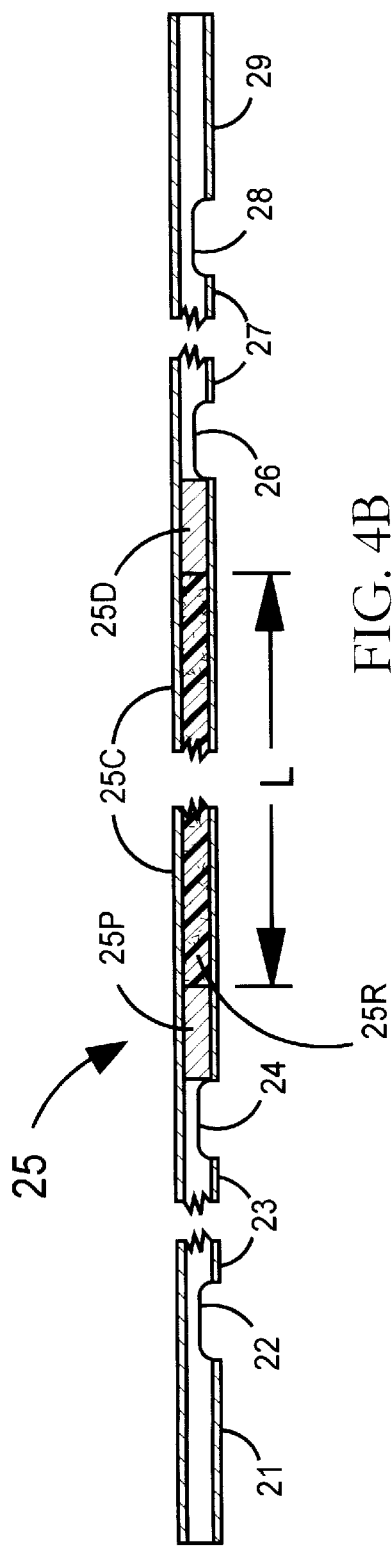
FIG. 4B is a longitudinal cross section of a longitudinal strut of the temporary radioisotope stent showing the location of the radioactive source and its distal and proximal radiopaque markers.

FIG. 3 is a longitudinal cross section showing both the proximal portion 40P and the distal portion 40D of the temporary radioisotope stent catheter system 10. The catheter system 10 consists of an inner shaft 11 having an interior lumen 12 which forms the passageway for a flexible guide wire 50, and an outer shaft 13 having an inner lumen 14 which serves as a passageway for the inner shaft 11. A temporary radioisotope stent 20 is situated at the distal portion 40D of the catheter system 10 as shown in FIG. 3. The temporary radioisotope stent 20 consists of a multiplicity of longitudinal struts 25 each having a central section 25C which, as seen in FIG. 4A, has a radioactive core 25R and a thin-walled outer cylindrical shell 25S. For arteries having a smaller diameter, as few as four longitudinal struts 25 might be used. For larger diameter arteries as many as 16 longitudinal struts 25 might be utilized. As seen in FIGS. 3 and 4B, each longitudinal strut 25 consists of a proximal section 21, a first flexible length 22, a proximal straight section 23, a second flexible section 24, a radioactive central section 25C, a third flexible section 26, a distal straight section 27, a fourth flexible section 28, and a distal section 29. Each proximal straight section 21 is fixedly attached to the outer surface at the distal end of the outer shaft 13. The distal sections 29 are fixedly attached to the distal radiopaque marker band 34.

When the catheter system 10 is advanced through the patient's arterial system, the position of the temporary radioisotope stent 20 is as shown by the solid lines in FIG. 3. After the stent is placed at the site of a dilated stenosis within an artery, the radial deployment operating means located at the proximal portion 40P of the catheter system 10 is used to expand the temporary radioisotope stent 20 in a manner shown by the dotted lines in FIG. 3. Although the proximal sections 21 and the distal sections 29 do not move when the stent 20 is radially expanded, the straight sections 23 and 27 move out as shown by elements 23', and 27'. The radioactive central sections 25C expand radially outward as shown by the element 25C'. It is conceived that the position of the temporary radioisotope stent 20 would normally be as shown by the dotted lines in FIG. 3 if not constrained by the inner shaft 11 and outer shaft 13. That is, the temporary radioisotope stent 20 would normally be urged to extend to the position as shown by the dotted lines in FIG. 3. When the temporary radioisotope stent 20 is deployed radially outward, the angle between the straight sections 23' and the radioactive central section 25C' form an angle "a" as shown in FIG. 3. A proximal radiopaque marker band 33 is located at the proximal end of the stent 20 and the distal radiopaque marker band 34 is located at the distal end of the stent 20. The two radiopaque marker bands 33 and 34 assist the doctor in properly placing the temporary radioisotope stent 20 at the site of a dilated arterial stenosis.

A gently tapered, elastomer, distal tip 30 is fixedly attached to both the distal end of the inner shaft 11 and the interior distal portion of the distal radiopaque marker band 34. A hole 11A cut through the wall of the inner shaft 11 near its distal end increases the holding force of the distal tip 30 onto the shaft 11. The gently tapered distal tip 30 is sufficiently flexible to enhance the capability of the catheter system 10 to maneuver through even a tortuous path in the coronary vasculature. The distal tip 30 could employ either or both a central lumen 31 which serves as a passageway for the guide wire 50 or a side passageway 32 which can be used for a guide wire 50. If the central passageway 31 is utilized, then the catheter system 10 will be an over-the-wire system. If the side passageway 32 is utilized, the catheter system 10 will have rapid exchange capability. The distal tip 30 could have both a central passageway 31 and a side passageway 32 thereby providing both over-the-wire and rapid exchange capability at the same time for the catheter system 10. For either an over-the-wire or a rapid exchange capability, the guide wire 50 would pass through the distal exit port 35 which is at the distal end of the distal tip 30. If rapid exchange capability is used, the guide wire 50 would also exit from the side of the distal tip 30 at the proximal exit port 36.

The proximal portion 40P of the catheter system 10 as shown in FIG. 3 utilizes an outer shaft adjustment screw 41 which cooperates with the adjustment nut 43 to move the inner shaft 11 in a longitudinal direction relative to the outer shaft 13. The longitudinal displacement of the inner shaft 11 relative to the outer shaft 13 adjusts the diameter to which the temporary radioisotope stent 20 can be radially expanded within a dilated arterial stenosis. As seen in FIG. 3, the angular rotation of the adjustment nut 43 relative to the outer shaft's adjustment screw 41 results in a controlled longitudinal displacement of the outer shaft 13 relative to the inner shaft 11.

Also seen at the proximal portion 40P of the catheter system 10 in FIG. 3, is an inner shaft distal screw 46 which is fixedly attached at the distal end of the inner shaft 11. After the adjustment nut 43 is screwed onto the outer shaft adjustment screw 41, the holding nut 47 is screwed onto the inner shaft distal end screw 46. When the holding screw 47 is in place, a cylindrical disk section at the proximal end of the adjustment nut 43 will be held between the surface 46P of the inner shaft distal end screw 46 and the distal surface 47D of the holding nut 47. Specifically, the annular surfaces 43D and 43P of the adjustment nut 43 are held between the surfaces 46P of the screw 46 and 47D of the holding nut 47. If it is desired to refurbish the catheter system 10 after it has been used within a human patient, the holding nut 47 can be removed and the adjustment nut 43 can be removed, and if the distal tip 30 is melted or otherwise removed, then the inner shaft 11 can be pulled out of the outer shaft 13 so that it can be carefully cleaned before reassembly into a new temporary radioisotope stent catheter system 10. It should also be noted that the holding nut 47 has an entry cone 51 to assist in the placement of the guide wire 50 through the inner shaft lumen 12. Furthermore, the O-ring 48 prevents blood from leaking around the guide wire 50, and the O-ring 42 prevents blood from leaking around the inner shaft 11.

FIG. 4A is a transverse cross section of a single longitudinal strut 25. The central section 25C of the longitudinal strut 25 contains a radioactive source 25R which is placed inside a thin-walled tubular shell 25S. Typical dimensions for the outer diameter of the cylindrical shell 25S would be between 0.1 and 0.5 mm, with a wall thickness between 0.01 and 0.2 mm. The typical material for the cylindrical shell 25S would be a stainless steel such as Type 316L or a shape memory metal alloy such as Nitinol.

FIG. 4B is a longitudinal cross section of a single longitudinal strut 25. The central section 25C would contain a radioactive source 25R having a length "L", which source 25R would have a proximal radiopaque cylindrical marker 25P just proximal to the radioactive source 25R and a cylindrical marker 25D placed just distal to the radioactive source 25R. The purpose of the radiopaque markers 25P and 25D is two-fold: firstly, the markers would clearly indicate the longitudinal extent of the radioactive source 25R; secondly, the radioactive markers can be used to provide a hermetic seal to completely enclose the radioactive source 25R within a metal structure. It should also be understood that a radioactive source could be alloyed into the metal of the central section 25C or placed onto its outer surface.

The material for the radioactive source 25R could be any isotope which is either a beta particle or gamma ray emitter. Ideally, the source 25R would be the isotope strontium-90 which, with its daughter product yttrium-90 is a pure beta particle emitter with a half-life of 28.5 years. Thus, the temporary radioisotope stent catheter system could be reusable. This would have the advantage of decreasing life cycle costs when one takes into account repeated usage. If the pure beta particle emitting isotope phosphorus-32 is used, the catheter system 10 might have a shelf life of only 4–6 weeks and it would not be reusable. If either Sr-90 or P-32 were used, at the time that the catheter system 10 is placed in a human patient it should have an activity between 2 and 100 milliCuries. The activity level of the temporary radioisotope stent and the diameter of the dilated stenosis determines the time period for placing the temporary radioisotope stent 20 at the site of the dilated stenosis. For example, a Sr-90 activity level of 10 milliCuries would allow an exposure time of approximately 5 minutes for a dilated stenosis having a diameter of 3.0 mm. Increasing activity level would decrease exposure time and greater diameters would also require greater exposure times to obtain the same radiation dose to the tissue at the site of the dilated stenosis.

Further to FIG. 4B, the flexible sections 22, 24, 26 and 28 could be implemented in a variety of ways. For example, instead of removing most of the perimeter of the tubular structure of the longitudinal strut 25 in order to achieve a high level of flexibility at specific positions along the longitudinal strut 25, one could use a cutting laser beam to remove metal in a spiral pattern at each of the positions 22, 24, 26, and 28 thereby forming a helical structure at each such site.

Such a helical structure would provide the desired flexibility where needed. Furthermore, straight cylindrical sections 21, 23, 25C, 27 and 29 could each be interconnected by a flexible elastomer in a cylindrical form that is placed inside the tubing of the longitudinal strut 25. Another way to provide flexibility would be to crush the tubing so as to be flat at the positions 22, 24, 26 and 28 of FIG. 4B.

To increase the capability of the distal portion of the catheter system for navigating through curved arteries, it is desirable to have increased flexibility at the distal portions of the inner shaft 11 and/or the outer shaft 13. One means for accomplishing increased flexibility for the thin-walled, elongated, cylindrical shell from which the inner shaft 11 (or the outer shaft 13) is made is illustrated in FIG. 4C.

Figure 4C:
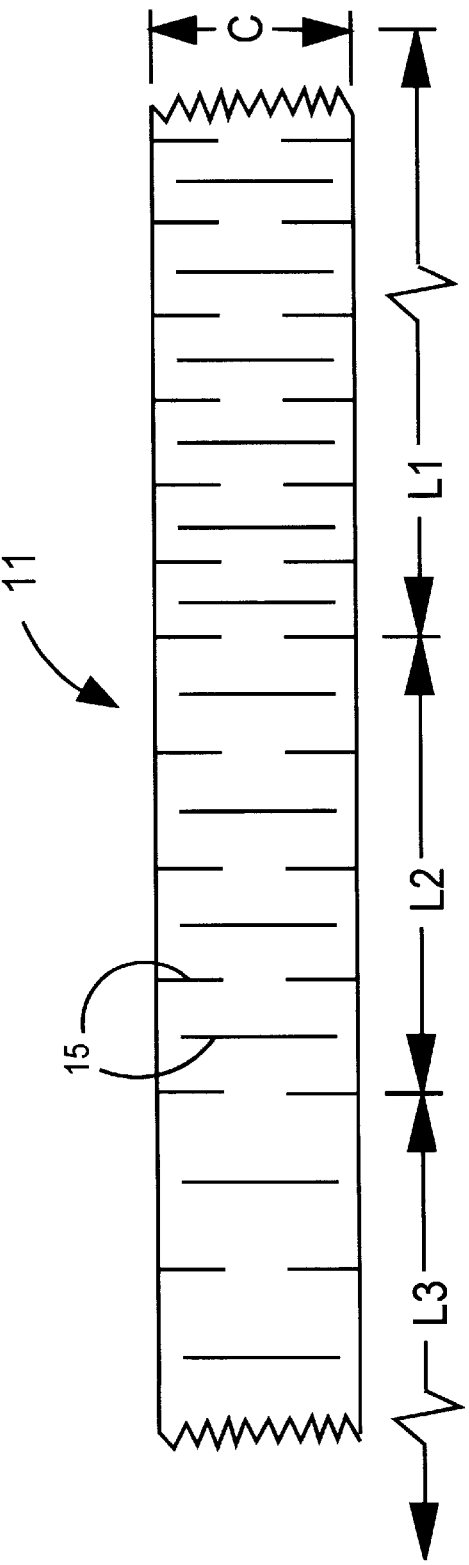
FIG. 4C is a layout view of a distal portion of the inner shaft of the catheter system.

Specifically, FIG. 4C is a layout view of a distal portion of the cylindrical inner shaft 11. This view would be seen if the inner shaft 11 was cut longitudinally and then opened up to form a flat, laid-out surface. From FIG. 4C we see that the circumference of the inner shaft 11 would be given by "C" as shown in FIG. 4C. Of course, $C=\pi \times d$, where d is the diameter of the inner shaft 11. As shown in FIG. 4C, a multiplicity of circumferential laser cuts which have an arc length of approximately 300 degrees would provide dramatically increased flexibility for either the inner shaft 11 or the outer shaft 13. These laser cuts would have a width of approximately 0.1 mm. The number of such cuts per unit length of the tube would increase as one moves in the distal direction, thereby providing ever increasing flexibility at the most distal portions of the inner shaft 11 or the outer shaft 13. Specifically, it can be seen that the number of laser cuts per unit length of the shaft 11 goes from the fewest cuts per unit length in section L3, to a greater number of cuts per unit length in section L2 and the greatest number of cuts per unit length in section L1 which is the most distal section shown in FIG. 4C.

A significant advantage in the design of the inner shaft 11 or the outer shaft 13 as indicated in FIG. 4C is that this design allows an extremely strong, thin-walled tubular structure to be used with either a push force or a pull force without substantially changing the length of those structures. This would not be the case if an elastomer tube were used for either the inner shaft 11 or the outer shaft 13. Also, it would not be true if the flexibility at the distal portion of the shaft's 11 and 13 was accomplished by making helical laser cuts in such tubing. Such a helical cut would experience a considerable change in length when a pull force was exerted on such a shaft design.

FIG. 5 is a longitudinal cross section of a distal portion of the temporary radioisotope stent catheter system 10 shown with the radioisotope stent 20" having its radially deployed longitudinal struts 25"0 deployed radially outward against the inner cylindrical surface of a dilated stenosis. FIG. 6 is a transverse cross section of the catheter system 10 showing central section 25C" of the longitudinal struts 25" deployed radially outward against the surface of the dilated stenosis. The section 23" is situated between the flexible sections 22" and 24" and the section 27" is situated between the flexible sections 26" and 28". FIG. 5 shows that the flexible sections 22", 24", 26" and 28" have each been appropriately bent so that the central section 25C" of the longitudinal strut 25" has moved out to make contact with the inner wall of the dilated stenosis. It should be understood that the radially expanded radioisotope stent 20" would also be effective if one or more or all central sections 25C" of the longitudinal struts 25" was not in actual contact with, but was in close proximity to, the inner wall of the dilated stenosis. In either case, the expanded temporary radioisotope stent 20" would be approximately centered within the dilated stenosis which is an extraordinary desirable attribute when applying catheter based radiation at the site of a dilated stenosis to prevent restenosis. As opposed to the centering means of the prior art devices as illustrated in FIGS. 2A and 2B, the design of the present invention as illustrated in FIGS. 5 and 6 can apply radiation in an optimum manner to the dilated stenosis. Specifically, the design of FIGS. 2A and 2B would not function at all in an 8 mm diameter vessel using a pure beta particle emitter such as P-32 because the beta particles from the P-32 would hardly reach the inner surface of the dilated stenosis and would certainly not reach the adventitia of the artery which is a principal source of smooth muscle cell proliferation which can cause restenosis of a dilated stenosis. Furthermore, the design of FIG. 5 requires a decreased radioisotope source strength as compared to the designs of either FIG. 1A or 2A. Therefore the design of FIG. 5 is safer to handle and can have a decreased cost for the radioisotope source.

Another important advantage which the catheter system 10 has when the temporary radioisotope stent 20" is expanded is that excellent perfusion of tissue distal to the stent 20" is achieved. This can be best envisioned by observing in FIG. 6 that there is a great deal of open space between the struts 27" of the expanded temporary radioisotope stent 20". FIG. 5 shows the direction of blood flow by the arrows 55 that are situated proximal to the stent 20" and the arrows 57 indicating the direction of blood flow distal to the stent 20". Since the perfusion of distal tissue is completely adequate when the temporary radioisotope stent 20" is fully radially expanded, the stent 20" can remain at the site of the dilated stenosis for as much time as is required to obtain an adequate dose of radiation to the tissue that has experienced dilatation.

Figure 7:
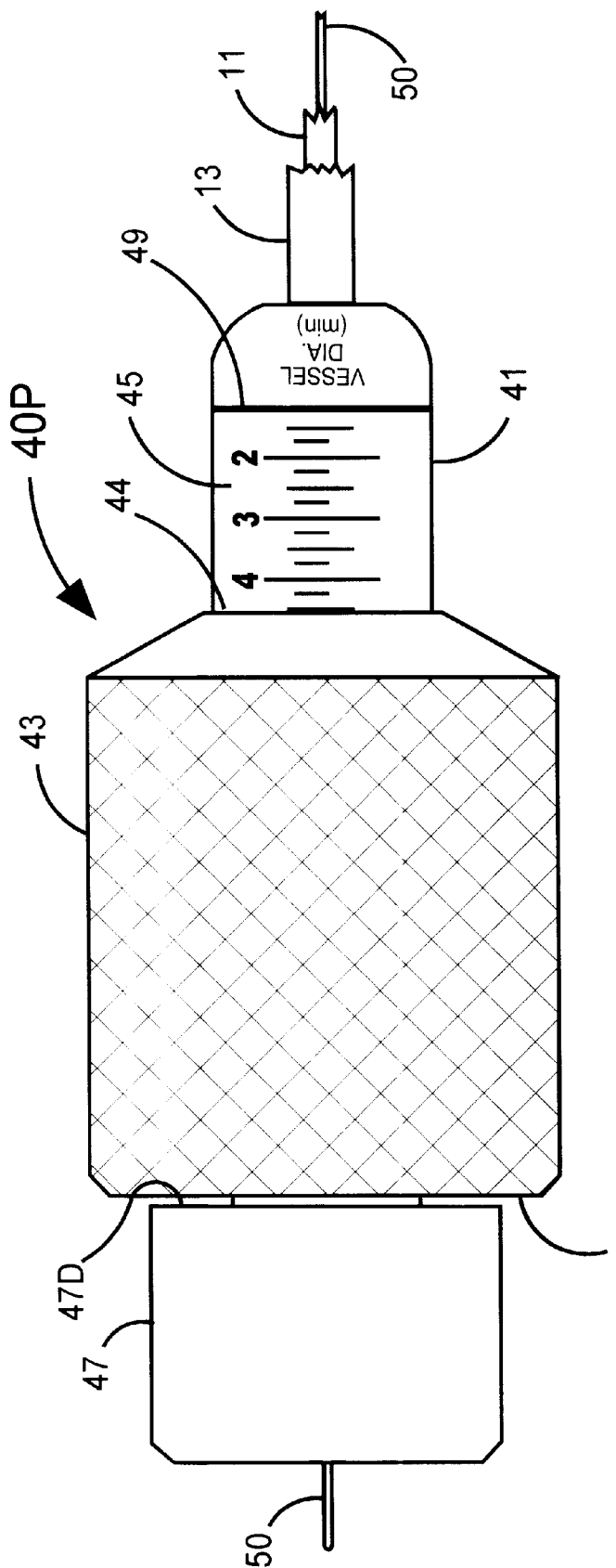
FIG. 7 is a top view of the proximal portion of the catheter system showing the operating means that is used for radial expansion and contraction of the temporary radioisotope stent.

FIG. 7 is a top view of the proximal end 40P of the temporary radioisotope stent catheter system 10 showing the holding nut 47 having a distal surface 47D, the adjustment nut 43 having a proximal surface 43P, and the outer shaft adjustment screw 41 having a stent diameter indicator scale 45. As shown in FIG. 7, the adjustment screw 43 has been screwed back until its leading edge 44 is over the 4.5 mm diameter mark of the indicator scale 45. This would provide a radial expansion of the temporary radioisotope stent 20" to a diameter of 4.5 mm. In order to move the catheter system 10 forward during insertion or to have it pulled out after the patient's dilated stenosis has received the appropriate radiation dose, the adjustment screw 43 would be screwed forward in a distal direction until its leading edge 44 was placed over the mark 49, which mark indicates that the stent 20 has been fully retracted to its smallest diameter. The diameter of the temporary radioisotope stent 20 as shown fully retracted in FIG. 3 would occur when the leading edge 44 is placed over the line 49.

Although a screw arrangement for moving the inner shaft 11 relative to the outer shaft 13 is shown in FIG. 3, it should be understood that a device that provides linear motion without a screw arrangement is also conceived. Furthermore, a fluidic operating system to provide a longitudinal displacement between the two shafts 11 and 13 is also envisioned.

Figure 9:
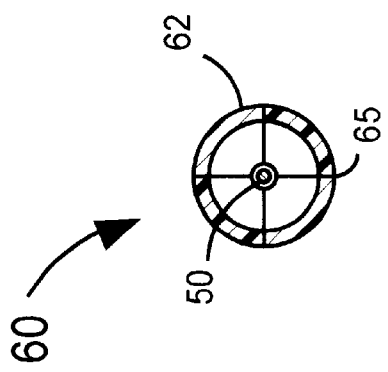
FIG. 9 is a transverse cross section of the sheath at section 9—9 of FIG. 8.
Figure 8:
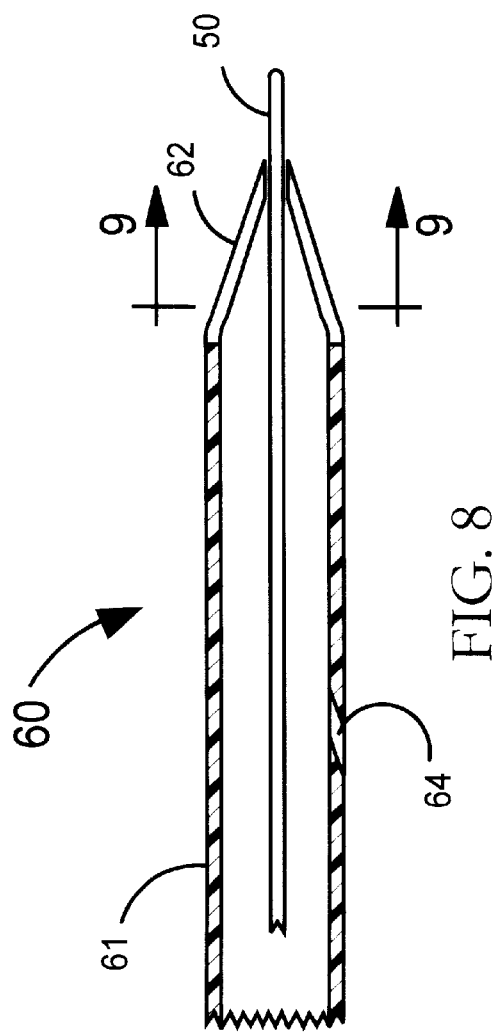
FIG. 8 is a longitudinal cross section of an elongated cylindrical sheath which can be percutaneously inserted into an artery and through which a temporary radioisotope stent catheter system can be inserted.

Although the temporary radioisotope stent catheter system 10 of the present invention is clearly usable as described herein, it is envisioned that for some dilated stenoses it may be advantageous to first place a sheath within the patient's vascular system through which sheath the catheter system 10 can be placed prior to the deployment of the temporary radioisotope stent 20. FIG. 8 illustrates the distal portion of an elongated, cylindrical sheath 60 having a cylindrical body 61 and an expandable, tapered distal tip 62. Also shown in FIG. 8 is a guide wire 50 shown in a position where it would be used if the catheter system 10 was advanced within the sheath 60 using the over-the wire technique. The proximal guide wire exit port 64 shown in FIG. 8 can be used to deliver the sheath 60 over the guide wire 50 in a rapid exchange mode. FIG. 9 is a transverse cross section of the expandable, tapered tip 62 particularly showing the four cuts 65 that allow the distal tip 62 to expand radially outward when the catheter system 10 would be pushed through it in a distal direction. Although four cuts 65 are shown in FIG. 9, as few as two cuts or as many as eight cuts are envisioned as a workable design to allow for the ready egress of the catheter system 10.

Figure 10:
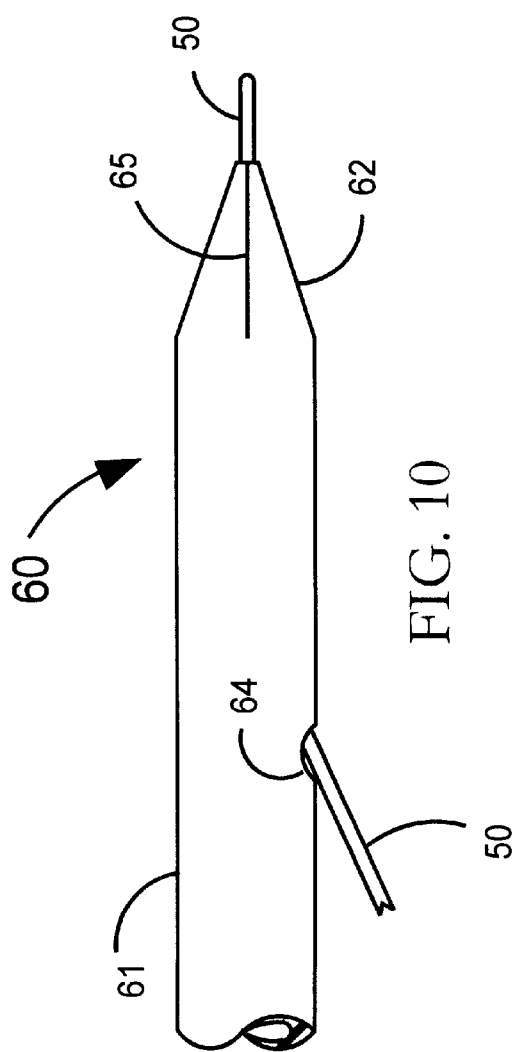
FIG. 10 is a side view of the sheath showing a slit at the gradually tapered distal section of the sheath and also showing a guide wire exiting the sheath in a manner to provide rapid exchange capability.

FIG. 10 is a top view of the sheath 60 showing the cylindrical body 61, the tapered distal tip 62 and a cut 65 with the guide wire 50 placed through the proximal exit port 64. As shown in FIG. 10, the sheath 60 would be capable of being delivered in the rapid exchange mode. Before the catheter system 10 could be placed through a sheath 60 when the sheath 60 is delivered in the rapid exchange mode, the guide wire 50 would have to be removed.

The sheath 60 as shown in FIGS. 8, 9, and 10 would typically have a diameter between 1 and 2 mm and a wall thickness between 0.1 and 0.3 mm. The material of the sheath 60 would typically be an elastomer such as polyurethane or PTFE.

Figure 11:
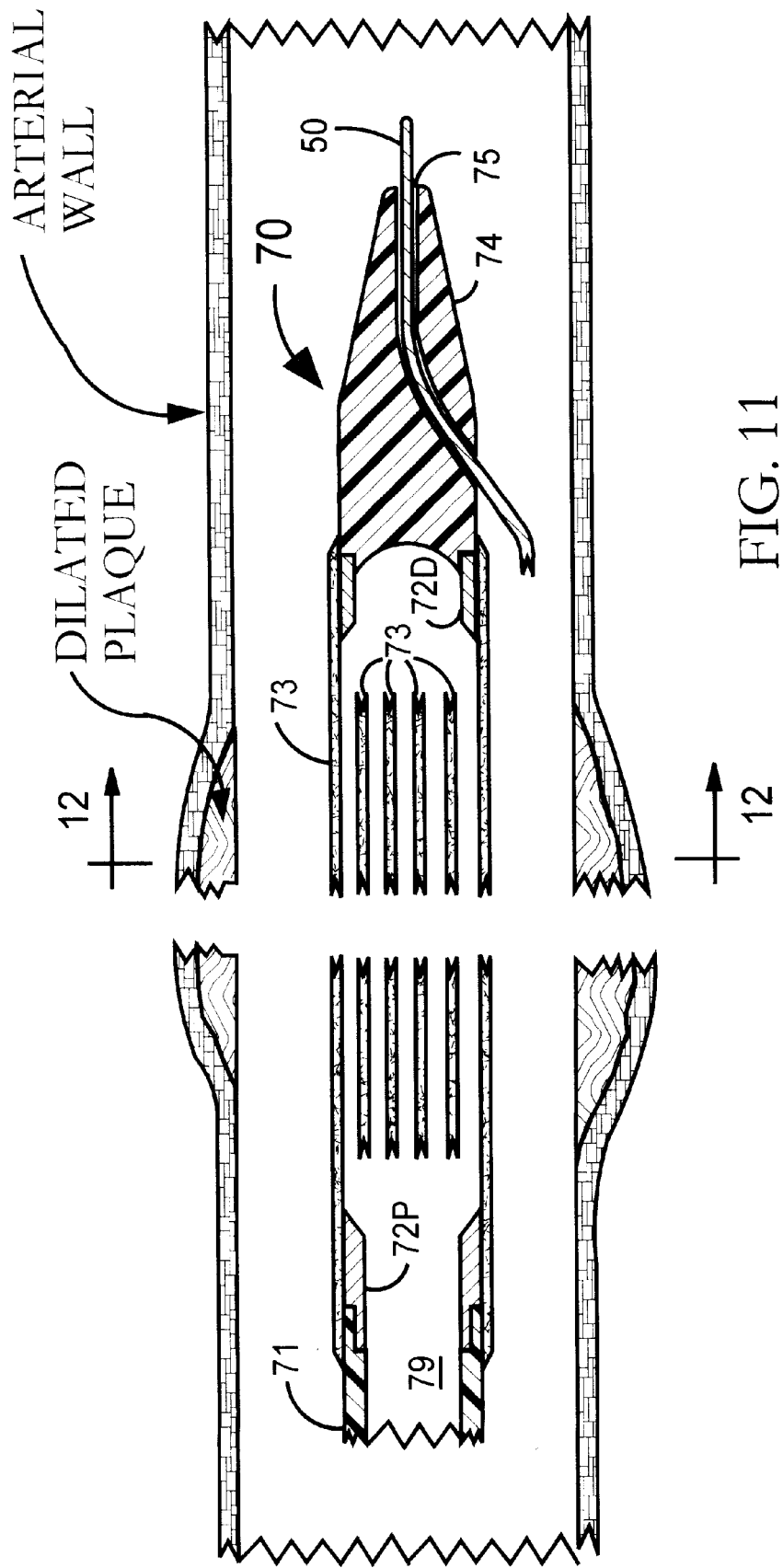
FIG. 11 is a longitudinal cross section of a distal portion of an alternative embodiment of a sheath to be used with the temporary radioisotope stent catheter system.

FIG. 11 is a longitudinal cross section of a proximal portion of an alternative embodiment of a sheath 70, which sheath has the capability for allowing blood to perfuse distal tissue even when a distal portion of the sheath is in its fully expanded state. FIG. 11 shows the perfusion sheath 70 in its pre-expanded state which is the state that it has when it is percutaneously inserted over the guide wire 50 until its distal portion is situated at the site of a dilated stenosis. In FIG. 11 we see that the perfusion sheath 70 has an elongated cylindrical, thin-walled tube 71 with central lumen 79 and an expandable section 73 having a proximal radiopaque marker band 72P and a distal radiopaque marker band 72D, and a gently tapered tip 74 which assists in navigating through the tortuous vasculature of the coronary arteries. The proximal and distal radiopaque marker bands 72P and 72D assist in positioning of the expandable section 73 of the sheath 70 at the site of the dilated stenosis.

Figure 12:
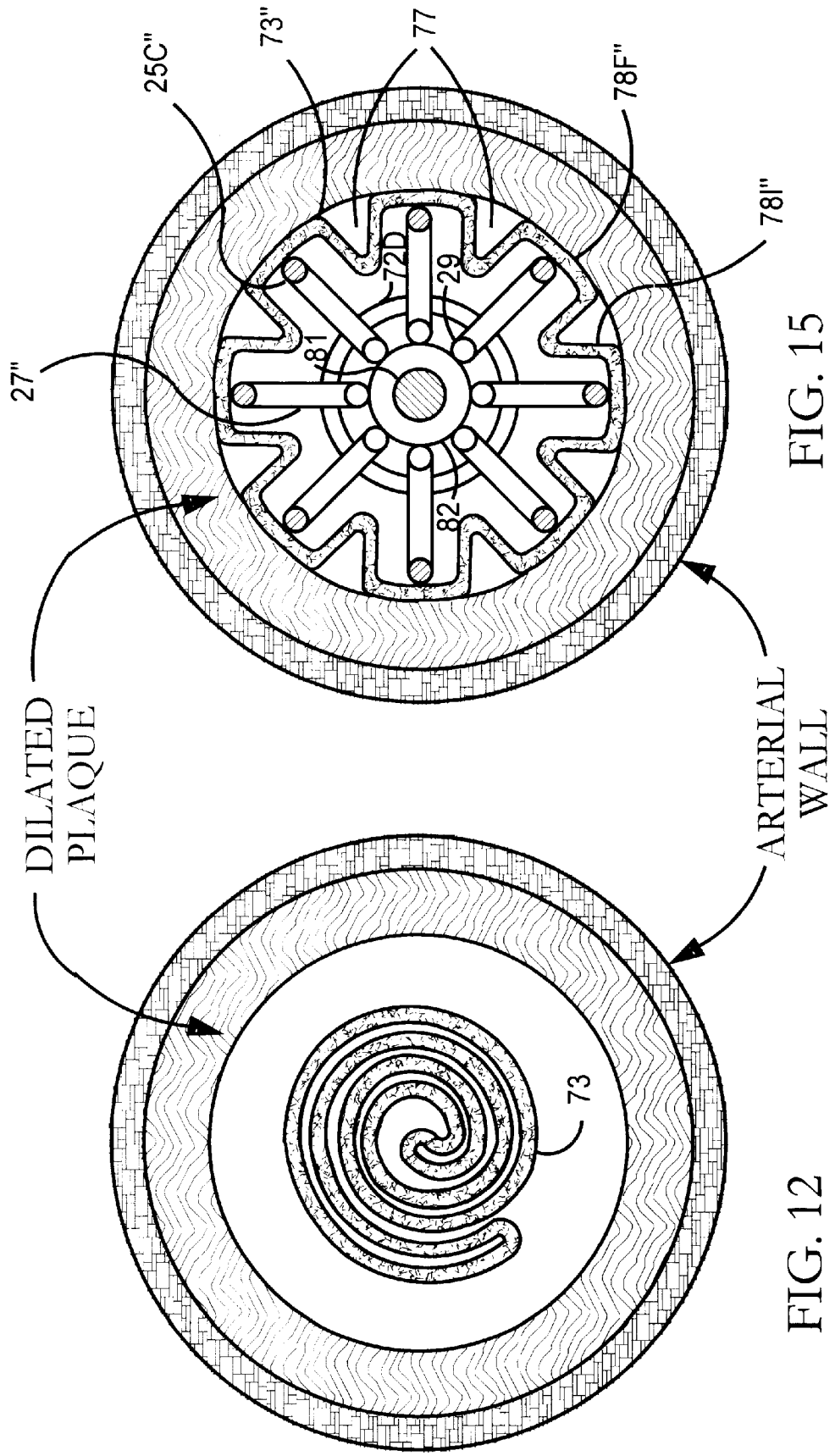
FIG. 12 is a transverse cross section of the sheath at section 12—12 of FIG. 11.

FIG. 12 is a transverse cross section of the expandable section 73 of the perfusion sheath 70 shown in its pre-expanded state. As seen in FIG. 12, in its pre-expanded state, the expandable section 73 is wrapped around like a jelly roll. It is also envisioned that the pre-expanded, expandable section 73 of the sheath 70 could be folded with a multiplicity of "wings" in a manner analogous to the way the balloon on a balloon angioplasty catheter is folded.

Figure 13:
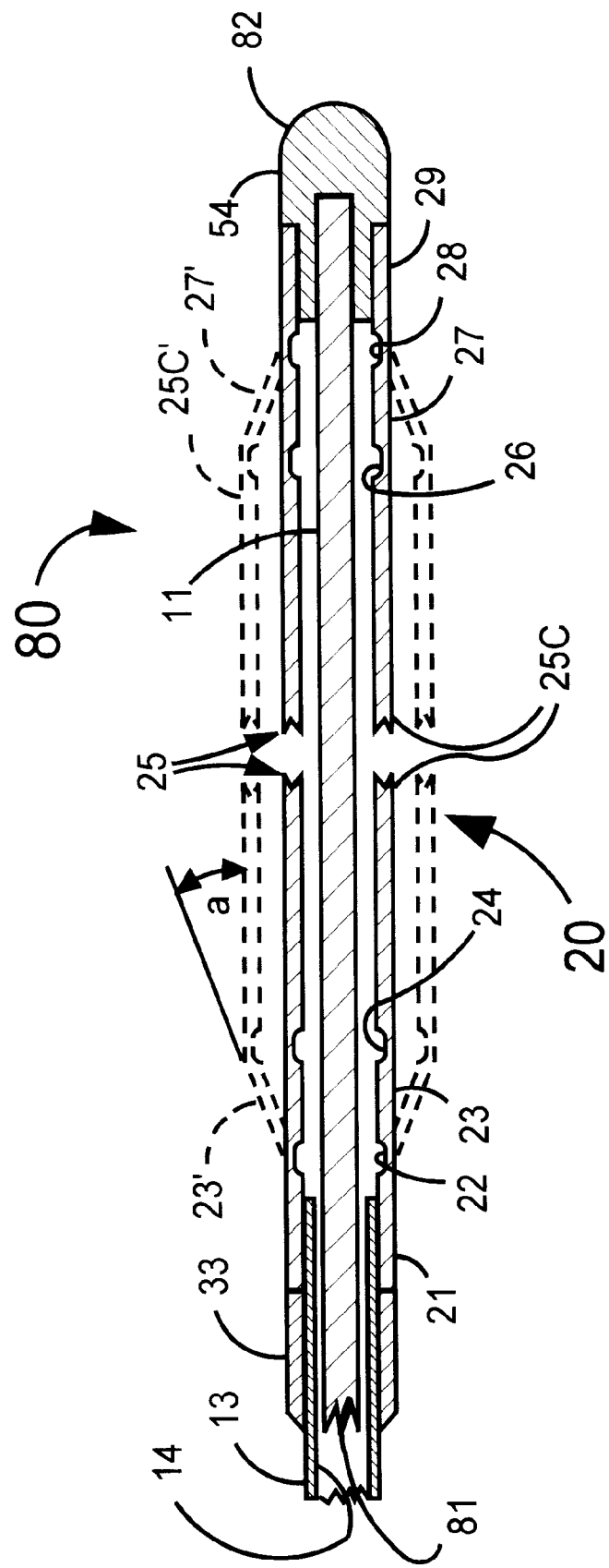
FIG. 13 is a longitudinal cross section of a distal portion of an alternative embodiment of the temporary radioisotope stent catheter system having a rounded distal tip.

FIG. 13 is a longitudinal cross section of an alternative embodiment of a distal portion of a temporary radioisotope stent catheter system 80. The proximal portion of the catheter system 80 is identical to that previously described in FIGS. 3 and 7. The distal portion of the catheter system 80 is slightly different at its distal end. Instead of a distal tip 30, the alternative embodiment of the catheter system shown in FIG. 13 has a short, rounded distal tip 82 which also serves as the distal radiopaque marker for the temporary radioisotope stent 20. In fact, this embodiment does not require a guide wire because it would be advanced through the previously placed sheath 70. Therefore, the inner shaft 11 could alternatively be a solid wire 81. It should be understood that the catheter system 80 operates in exactly the same manner as the catheter system 10 of FIG. 3 except that the catheter system 80 is designed to be advanced within a previously placed sheath such as the perfusion sheath 70 of FIG. 11.

Figure 14:
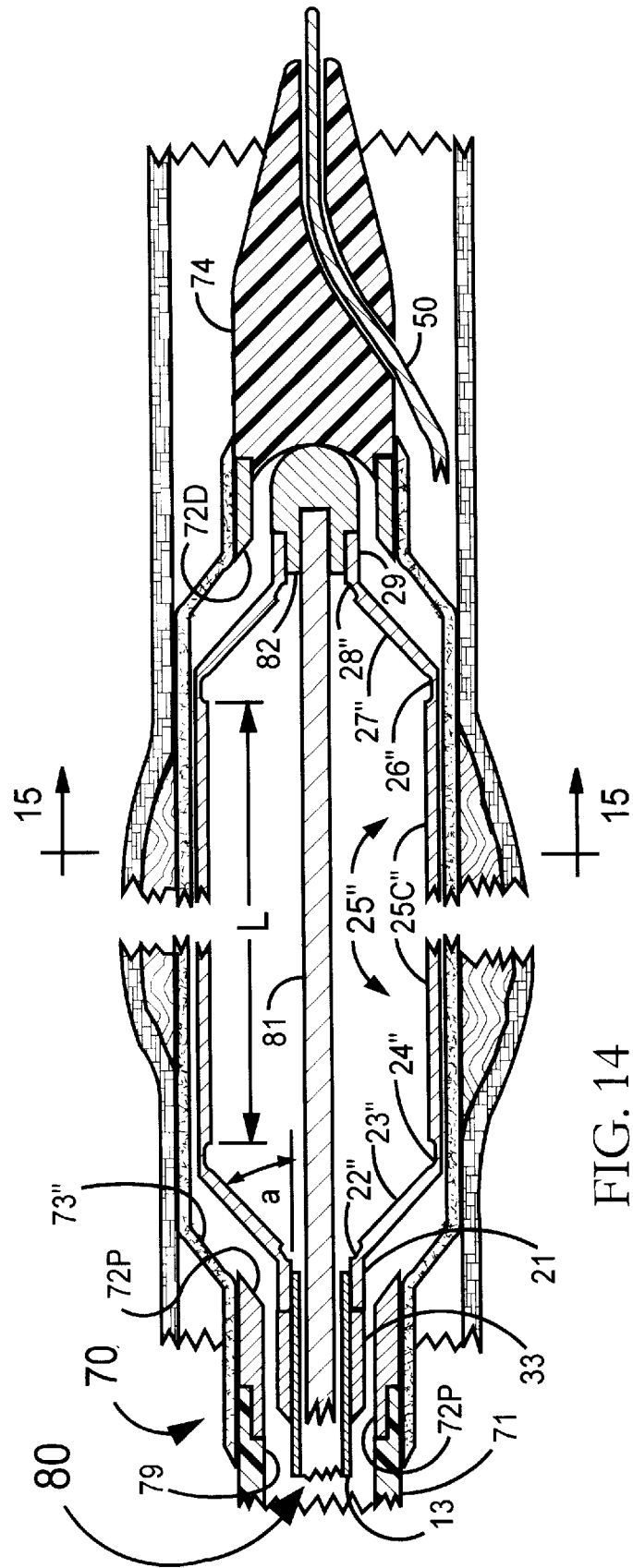
FIG. 14 is an longitudinal cross section of the distal portions of the alternative embodiment of a perfusion sheath and temporary radioisotope stent catheter system.
Figure 16:
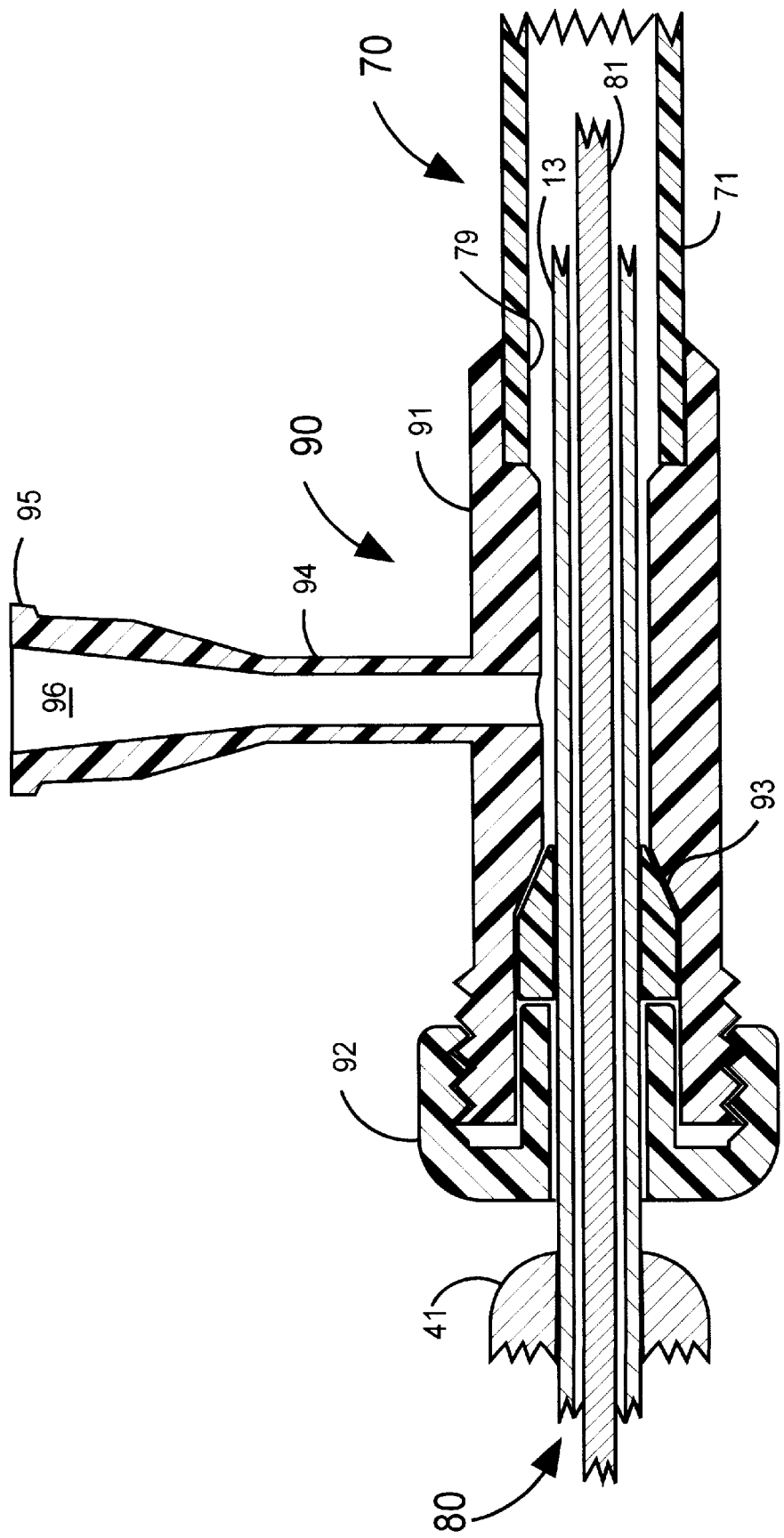
FIG. 16 is a longitudinal cross section of the proximal portion of the alternative embodiment of the perfusion sheath illustrating a Tuohy-Borst "Y" adaptor at the proximal portion of the sheath.

FIG. 14 is a longitudinal cross section of the distal portions of the perfusion sheath 70 and the catheter system 80. The expanded section 73" of the perfusion sheath 70 is shown in contact with the inner wall of the dilated stenosis. The transverse cross section of the expanded section 73" of the sheath 70 is illustrated in FIG. 15. The contour of the expanded section 73" as shown in FIG. 15 is pre-formed to have flat sections 78F" and indented sections 78I". The indented sections 78I" allow the longitudinal flow of blood through the passageways 77 so as to perfuse distal tissue during the time period that the temporary radioisotope stent 20" is expanded as shown in FIG. 14. This expanded state of the expanded section 73" is achievable by means of the Tuohy-Borst "Y" adaptor 90 as shown in FIG. 16 It is desirable though not required that the expansion of the expandable sheath section 73" be accomplished prior to the insertion of the catheter system 80. The solid rod shaft 81 in FIGS. 14 and 15 is used to push the catheter system through the previously placed sheath 70.

As seen in FIG. 15, the radially outward deployed, radioactive longitudinal struts 25C" are in contact with the inner surface of the expanded section 73" of the sheath 70. The wall thickness of the expanded section 73" would typically be on the order of 0.1 mm, and since the material of the expanded portion 73" would be an elastomer having a comparatively low density, the expanded section 73" would not significantly decrease the level of radiation felt by the tissue of the dilated stenosis. However, unlike the radioisotope stent described by Fischell in U.S. Pat. No. 5,059,166, the radioisotope stent 20 shown in FIGS. 14 and 15 is not in direct contact with the tissue of the dilated stenosis. This small but finite separation can reduce a "hot spot" of irradiation which might otherwise occur when the struts of a radioisotope stent are in actual contact with or imbedded into the tissue of the dilated stenosis. Thus it is envisioned that a radioisotope stent having a small but finite separation between the radioisotope source and the tissue of the dilated stenosis may have some significant advantage.

FIG. 16 is a longitudinal cross section of the proximal portion of the perfusion sheath 70 showing the tube 71 having an inner lumen 79 and a Tuohy-Borst "Y" adaptor 90. The Tuohy-Borst "Y" adaptor 90 has a main body 91, an adjustable nut 92, an elastomer seal 93 and a side arm 94 having a central lumen 96 and a Luer fitting 95 at the proximal end of the side arm 94. The lumen 96 is in fluid communication with the lumen 79 of the sheath 70. By means of the Luer fitting 95, a syringe (not shown) can be used to inflate and deflate the expandable section 73 of the sheath 70. As previously described, the expandable section 73 would be advanced through the vessel of the human body in its pre-expanded state as shown in FIGS. 11 and 12. The expanded section 73" would be formed by inserting fluid under pressure through the Luer fitting 95. After the expanded section 73" has been formed, the catheter system 80 would be advanced until its distal tip 84 is in contact with the proximal surface of the tapered tip 74 of the sheath 70. The operating means at the proximal portion of the catheter system 80 would then be used to radially expand the temporary radioisotope stent struts 25C" to be as shown in FIGS. 14 and 15. Once the temporary radioisotope stent struts 25C" have been expanded, the pressure within the expanded section 73" of the sheath 70 would be reduced to be below diastolic blood pressure by utilizing either ambient pressure within the lumen 79 or by creating a negative pressure using suction. This results in the external perimeter of the expanded section 73" assuming the shape as shown in FIG. 15 with indented passageways 77 through which the blood can flow to tissue that lies distal to the expanded section 73". Thus, perfusion of distal tissue is achievable which allows the temporary radioisotope stent 25" to irradiate the dilated stenosis for an extended period of time without any adverse effect being felt by the patient.

After the period of irradiation is terminated, the operating means at the proximal portion of the catheter system 80 is used to radially contract the temporary radioisotope stent 25 and then the catheter system 80 can be removed from the sheath 70 and from the patient's body. The sheath 70 can then be contracted by placing a negative fluid pressure through the side arm 24 thereby contracting the expandable section 73 of the sheath 70. The sheath 70 can then be removed from the patient's body, and finally the guide wire 50 is removed thereby concluding the catheter based irradiation of the dilated stenosis.

Figure 17:
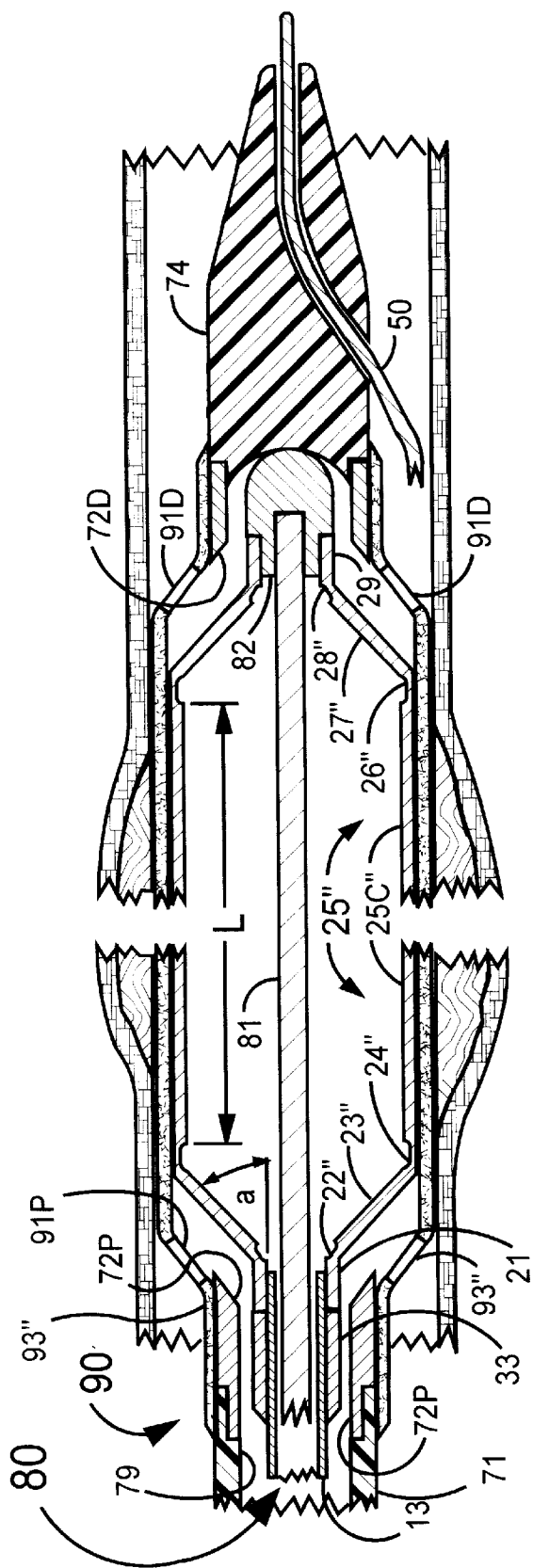
FIG. 17 is a longitudinal cross section of a distal portion of a second alternative embodiment of a temporary radioisotope stent catheter system having an expandable section of the sheath that includes holes that allow blood to flow through that portion of the sheath.
Figure 18:
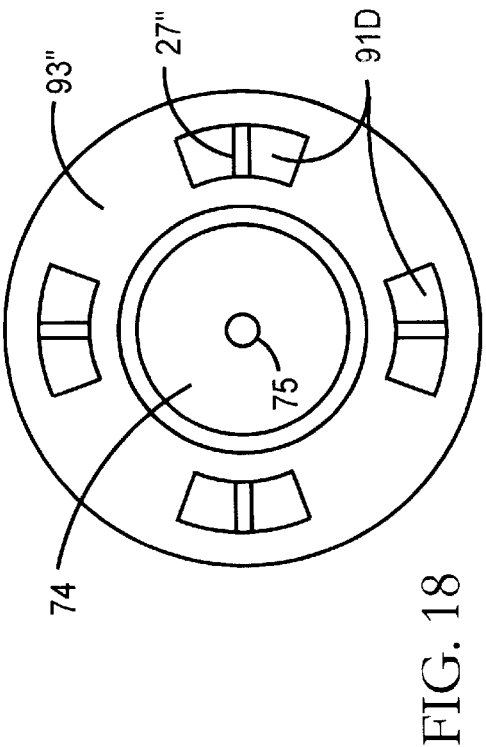
FIG. 18 is an end view of the expandable section of the sheath of FIG. 17 showing the arrangement of a multiplicity of holes through which the blood can flow.

FIG. 17 is another alternative embodiment of the present invention that allows blood to flow through a set of proximal and distal holes in the expandable section of the sheath 90, which blood makes contact with the temporary radioisotope stent struts 25". Specifically, the sheath 90 has an expandable section 93" that has a multiplicity of proximal holes 91P and distal holes 91D. FIG. 18 is a front end view of the expandable section 93" of the sheath 90 which shows a typical arrangement for the distal holes 91D. FIG. 18 also shows through the holes 91D the deployed straight sections 27" and also shows the distal tip 74 which has a distal guide wire exit port 75. Although FIG. 18 shows a total of four holes, it should be understood that as few as one hole could be used on each end of the expandable section 93" of the sheath 90 or several hundred holes could be used if the expandable section 93" was formed from a porous material.

It should also be understood that for all embodiments of the present invention that utilize a sheath, that the sheath would first be advanced until the expandable portion of the sheath was at the site of the dilated stenosis, and then the temporary radioisotope stent catheter system would be advanced within the sheath until the radioactive section of the stent struts was also situated at the site of the dilated stenosis.

It should also be understood that the present invention envisions a radioisotope stent that can be used independent of its attachment to a catheter system. Specifically it is envisioned that the temporary radioisotope stent 20 as shown in FIGS. 3 or 5 or 14 and as described herein teaches the principle that a permanently implanted radioisotope stent could be used in which the radioactive source is isolated from the inner wall of the dilated stenosis by either a thin piece of metal or a thin plastic membrane or both.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. A temporary radioisotope stent catheter system for applying radiation at the site of a dilated stenosis within a vessel of the human body, the catheter system comprising:

an elongated, cylindrical, inner shaft having a proximal end and a distal end;

an elongated, cylindrical, thin-walled outer shaft having a proximal end and a distal end, the outer shaft being situated coaxially around the inner shaft and being adapted to move slideably relative to the inner shaft;

a temporary radioisotope stent having a multiplicity of longitudinal struts, each longitudinal strut including a radioactive source, the radioactive source having the capability for irradiating the tissue of the dilated stenosis when the longitudinal struts are deployed radially outward so that at least one of the struts is in contact with the inner surface of the dilated stenosis, the temporary radioisotope stent also having a proximal end that is fixedly attached to the distal end of the outer shaft and a distal end that is fixedly attached to the distal end of the inner shaft; and a temporary radioisotope stent operating means that is adapted to move the inner shaft in a longitudinal direction relative to the outer shaft, the temporary radioisotope stent being deployed radially outward when the inner shaft is moved in a proximal direction relative to the outer shaft and the temporary radioisotope stent being retracted radially inward when the inner shaft is moved in a distal direction relative to the outer shaft.

2. The catheter system of claim 1 wherein the inner shaft is a solid wire.

3. The catheter system of claim 1 wherein there are at least eight longitudinal struts.

4. The catheter system of claim 1 wherein there are at least four longitudinal struts.

5. The catheter system of claim 1 wherein the radioactive source is a beta particle emitter.

6. The catheter system of claim 5 wherein the beta particle emitter is strontium-90.

7. The catheter system of claim 5 wherein the beta particle emitter is yttrium-90.

8. The catheter system of claim 5 wherein the beta particle emitter is phosphorous-32.

9. The catheter system of claim 1 wherein the radioactive source is a low energy x-ray emitter.

10. The catheter system of claim 1 wherein at least that part of the longitudinal strut that contains the radioactive source is a thin-walled cylinder.

11. The catheter system of claim 1 wherein the radioactive source has a proximal end and a distal end and has one radiopaque marker placed at the source's proximal end and a second radiopaque marker placed at the source's distal end.

12. The catheter system of claim 1 wherein there is one radiopaque marker band placed at the proximal end of the temporary radioisotope stent and one radiopaque marker band placed at the distal end of the temporary radioisotope stent.

13. The catheter system of claim 1 wherein the catheter system includes a tapered distal tip to enhance insertion through the vascular system of the human body.

14. The catheter system of claim 1 wherein the distal tip has a through hole for insertion over a guide wire for over-the-wire insertion of the catheter system.

15. The catheter system of claim 1 wherein the distal tip has a proximal guide wire exit port by means of which rapid exchange capability is obtainable for the catheter system.

16. The catheter system of claim 1 wherein each longitudinal strut consists of a multiplicity of comparatively rigid sections and a multiplicity of flexible sections and a central section which is comparatively rigid, these sections being adapted to cause radial expansion of the central section when the inner shaft is longitudinally displaced in a proximal direction relative to the outer shaft.

17. The catheter system of claim 1 wherein the operating means includes an inner shaft distal screw to which is joined a holding nut.

18. The catheter system of claim 1 wherein the operating means includes a threaded outer shaft adjustment screw and a threaded adjustment nut.

19. The catheter system of claim 18 wherein the outer shaft adjustment screw includes a stent diameter indicator scale that indicates the diameter to which the temporary radioisotope stent has been radially expanded.

20. The catheter system of claim 18 wherein the longitudinal position of the inner shaft is adjustable relative to the outer shaft by means of the threaded adjustment nut.

21. The catheter system of claim 20 wherein the threaded adjustment nut has a leading edge and the diameter of the temporary radioisotope stent is indicated by the position of the leading edge of the threaded adjustment nut relative to a stent diameter indicator scale that is fixedly attached to the proximal end of the outer shaft.

22. The catheter system of claim 1 wherein the inner shaft and the outer shaft are each thin-walled metal tubes.

23. The catheter system of claim 22 wherein the metal of the metal tubes is stainless steel.

24. The catheter system of claim 22 wherein the metal of the metal tubes is Nitinol.

25. The catheter system of claim 22 wherein at least one of the metal tubes is cut through in such a manner as to increase the longitudinal flexibility of that tube.

26. The catheter system of claim 22 wherein the metal tube forming the inner shaft and the metal tube forming the outer shaft are both cut through in such a manner as to increase longitudinal flexibility.

27. The catheter system of claim 22 wherein at least one of the metal tubes is cut through in such a manner that the more distal sections of that tube have a greater longitudinal flexibility as compared to the flexibility of a more proximal section of the at least one tube.

28. A temporary radioisotope stent catheter system for the treatment of a dilated stenosis in a vessel of a human body, the catheter system having a proximal portion that is adapted to be placed external to the human body and a distal portion that is adapted to be placed within the vessel of the human body at the site of the dilated stenosis, the distal portion of the catheter system including a radioactive, radially expandable, temporary radioisotope stent, the proximal portion of the catheter system having an operating means adapted to radially expand the temporary radioisotope stent, the operating means including a stent diameter indicator scale that indicates the diameter to which the operating means has expanded the temporary radioisotope stent.

29. The catheter system of claim 28 wherein the temporary radioisotope stent includes a beta particle emitting isotope.

30. The catheter system of claim 29 wherein the isotope is strontium-90.

31. The catheter system of claim 29 wherein the isotope is yttrium-90.

32. The catheter system of claim 29 wherein the isotope is phosphorous-32.

33. The catheter system of claim 28 wherein the catheter system includes a tapered distal tip having a proximal end and a distal end and a lumen through which a guide wire can be slideably placed, the distal tip also including a distal guide wire exit port located at the distal end of the distal tip through which the guide wire exits from the catheter system.

34. The catheter system of claim 33 wherein the guide wire lumen is centrally located and extends throughout the entire length of the distal tip thereby providing an over-the-wire capability for the catheter system.

35. The catheter system of claim 33 wherein the guide wire lumen in the distal tip has a proximal guide wire exit port located at the side of the distal tip near the proximal end of the distal tip thus providing a rapid exchange capability for the catheter system.

36. A temporary radioisotope stent catheter system for the irradiation of a dilated stenosis in a vessel of a human body, the catheter system comprising:

a flexible guide wire;

a sheath in the form of an elongated, cylindrical, hollow, elastomer tube; and a temporary radioisotope stent catheter system having a proximal portion and a distal portion, the proximal portion being adapted to remain exterior to the human body and the distal portion being adapted to be placed through the sheath and into the vessel of the human body, the catheter system having a radioactive temporary radioisotope stent located at the distal portion of the catheter system, the temporary radioisotope stent being adapted to be advanced through the sheath and into the vessel of the human body, the catheter system also being adapted to place the temporary radioisotope stent at the site of the dilated stenosis within the vessel, the proximal portion of the catheter system having an operating means that is adapted to cause the radial expansion of the temporary radioisotope stent to a specific, pre-determined diameter that is approximately equal to the inside diameter of the dilated stenosis.

37. A method for irradiating a dilated stenosis in a vessel of a human body, the method comprising the following steps:

(a) advancing a temporary radioisotope stent that is located at a distal portion of a catheter system until the temporary radioisotope stent is situated at the site of the dilated stenosis in the vessel of the human body, the position of the temporary radioisotope stent being determined from one radiopaque marker band located proximal to the temporary radioisotope stent and one radiopaque marker band located just distal to the temporary radioisotope stent;

(b) actuating an operating means located at the proximal portion of the catheter system so as to expand the temporary radioisotope stent radially outward until the inside diameter of the temporary radioisotope stent is approximately equal to the diameter of the dilated stenosis;

(c) allowing a radioactive source which is formed as part of the temporary radioisotope stent to remain situated at the site of the dilated stenosis until a predetermined radiation dose has been received by the tissue of the dilated stenosis;

(d) adjusting the operating means at the proximal portion of the catheter system so as to cause the temporary radioisotope stent to be radially contracted; and (e) removing the catheter system from the vessel of the human body.

38. A temporary radioisotope stent catheter system for applying radiation at the site of a dilated stenosis within a vessel of the human body, the catheter system comprising:

an elongated catheter having a proximal portion and a distal portion and having a radially expandable temporary radioisotope stent situated at the distal portion of the catheter and a temporary radioisotope stent operating means situated at the proximal portion of the catheter, the operating means being adapted to radially increase and radially decrease the diameter of the temporary radioisotope stent; and an elongated perfusion sheath situated co-axially around the elongated catheter, the sheath having a proximal portion and a distal portion and also having an expandable section located at the distal portion of the sheath, the expandable section of the sheath having a pre-expanded state and an expanded state, the expandable section when in its expanded state being adapted to allow blood flow through the vessel at the site of the expandable section of the sheath.

39. The catheter system of claim 38 wherein the sheath forms an enclosure that prevents the blood from making contact with the catheter.

40. The catheter system of claim 38 wherein the expandable section of the sheath when in its expanded state allows blood to flow between the outer surface of the expandable section and the inner surface of the dilated stenosis.

41. The catheter system of claim 38 wherein the expandable section of the sheath includes at least one distal hole and one proximal hole which holes allow blood to pass through the expandable section so as to perfuse tissue that is located distal to the site of the expandable section of the sheath.

42. A radioisotope stent in the form of a thin-walled cylindrical structure, the radioisotope stent being adapted to irradiate a dilated stenosis in a vessel of a human body, the dilated stenosis having an interior, generally cylindrical surface, the radioisotope stent consisting of a multiplicity of metal struts that are placed in close proximity to the inner surface of the dilated stenosis, the struts including a radioactive source which radioactive source does not come in direct contact with the inner surface of the dilated stenosis.

43. The radioisotope stent of claim 42 wherein a metal structure prevents the radioactive source from being in contact with the inner surface of the dilated stenosis.

44. The radioisotope stent of claim 42 wherein an elastomer material is situated between the radioactive source of the radioisotope stent and the interior, generally cylindrical surface of the dilated stenosis thereby preventing the radioactive source from making direct contact with the inner surface of the dilated stenosis.

* * * * *